United States Patent
Sugiura (10) Patent No.: US 8,313,780 B2
(45) Date of Patent: Nov. 20, 2012

(54) SILVER-BASED INORGANIC ANTIMICROBIAL AGENT, METHOD FOR PREPARING THE SAME AND ANTIMICROBIAL PRODUCT

(75) Inventor: Koji Sugiura, Naogya (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 13/321,322

(22) PCT Filed: May 20, 2010

(86) PCT No.: PCT/JP2010/058502

§ 371 (c)(1),
(2), (4) Date: Nov. 18, 2011

(87) PCT Pub. No.: WO2010/134566

PCT Pub. Date: Nov. 25, 2010

(65) Prior Publication Data

US 2012/0070509 A1    Mar. 22, 2012

(30) Foreign Application Priority Data

May 21, 2009    (JP) .................................. 2009-122625

(51) Int. Cl.
*A61P 31/04* (2006.01)
*A01N 59/26* (2006.01)
*A01P 1/00* (2006.01)

(52) U.S. Cl. ........................................ 424/604; 424/400
(58) Field of Classification Search ........................ None
See application file for complete search history.

(56) References Cited

U.S. PATENT DOCUMENTS

2010/0221360 A1    9/2010 Sugiura et al.
2010/0272828 A1    10/2010 Sugiura

FOREIGN PATENT DOCUMENTS

| JP | 60-239313 | A |   | 11/1985 |
|---|---|---|---|---|
| JP | 4-275370 | A |   | 9/1992 |
| JP | 5-17112 | A |   | 1/1993 |
| JP | 6-48713 | A |   | 2/1994 |
| JP | 2008-74778 | A |   | 4/2008 |
| JP | 2008-74781 | A |   | 4/2008 |
| JP | 2008-074778 |   | * | 4/2012 |
| WO | WO 2009/044477 | A1 |   | 4/2009 |
| WO | WO 2009/044478 | A1 |   | 4/2009 |

OTHER PUBLICATIONS

Hong, "Crystal Structures and Crystal Chemistry in the system Na1+xZr2Six P3-xO12", Mat. Res. Bull., vol. 11, No. 2, 1976, pp. 173-182.
International Search Report for PCT/JP2010/058502 dated Jun. 22, 2010.
Jager et al., "31P MAS NMR Study of the NASICON System Na1+4yZr2-y(PO4)3", Chemical Physics Letters, Sep. 30, 1988, vol. 150, No. 6, pp. 503-505.
Jager et al., "31P and 29Si NMR Investigations of the Structure of NASICON-Compounds" Experimentelle Technik der Physik 36, 1988, 4/5, pp. 339-348.

* cited by examiner

*Primary Examiner* — Scott Long
*Assistant Examiner* — Sarah Alawadi
(74) *Attorney, Agent, or Firm* — Birch, Stewart, Kolasch & Birch, LLP

(57) ABSTRACT

Disclosed is a silver-based inorganic antimicrobial agent which exhibits superior heat resistance, chemical resistance, processability and long-lasting waterproofness.
The present invention was completed based on the finding that the problems can be solved by a silver-based inorganic antimicrobial agent represented by the following Formula (1) containing zirconium pyrophosphate ($ZrP_2O_7$).

$$Ag_aM_bZr_cHf_d(PO_4)_3 \cdot nH_2O \qquad (1)$$

(In Formula (1), M is at least one ion selected from an alkali metal ion, an ammonium ion, a hydrogen ion and an oxonium ion, a, b, c and d are positive numbers satisfying $1.75 < (c+d) < 2.2$ and $a+b+4(c+d)=9$, and n is 2 or less).

17 Claims, 2 Drawing Sheets

FIG.1

SILVER-BASED INORGANIC ANTIMICROBIAL AGENT, METHOD FOR PREPARING THE SAME AND ANTIMICROBIAL PRODUCT

TECHNICAL FIELD

The present invention relates to a silver-based antimicrobial agent containing silver-supporting zirconium phosphate as a main component, a method for preparing the same and an antimicrobial product in which the antimicrobial agent is incorporated by a kneading or application process. The antimicrobial agent of the present invention is a silver-based inorganic antimicrobial agent which exhibits superior waterproofing property, heat resistance, chemical resistance and processability, and excellent sustained-release of silver ions, thus having antimicrobial effects with long-lasting waterproofness, as compared to conventional antimicrobial agents.

BACKGROUND ART

Recently, zirconium phosphate-based inorganic ion exchangers have been used for a variety of applications based on the characteristics thereof. Zirconium phosphate-based inorganic ion exchangers include amorphous zirconium phosphates and crystalline zirconium phosphates including a 2-dimensional layered structure or a 3-dimensional network structure. Among these, hexagonal zirconium phosphates having a 3-dimensional network structure exhibit superior heat resistance, chemical resistance, radiation resistance and low thermal expansion properties and the like and are thus being applied to immobilization of radioactive wastes, solid electrolytes, gas adsorbing/separating agents, catalysts, raw materials for antimicrobial agents and the like.

Various hexagonal zirconium phosphates are currently known. For example, $A_x NH_{4(1+x)} Zr_2(PO_4)_3 \cdot nH_2O$ is disclosed in PTL (Patent Literature) 1, $AZr_2(PO_4)_3 \cdot nH_2O$ is disclosed in PTL 2, and $H_n R_{(1-n)} Zr_2(PO_4)_3 \cdot mH_2O$ is disclosed in PTL 3.

In addition, zirconium phosphates having different ratios of Zr and P are also known. For example, $Na_{1+4x} Zr_{2-x}(PO_4)_3$, is disclosed in NPL 1, and $Na_{1+2x} Mg_x Zr_{2-x}(PO_4)_3$ is disclosed in NPL (Non-patent Literature) 1 and 2. $Na_{1+x} Zr_2 Si_x P_{3-x} O_{12}$ is disclosed in NPL 2 and 3.

Methods for synthesizing hexagonal zirconium phosphates include a high-temperature heating synthesis method in which synthesis is carried out by mixing solid-form powder raw materials and then heating the mixture at a high temperature of 1,000° C. or more using a heating furnace, a hydrothermal method in which synthesis is carried out by mixing raw materials dissolved in water or mixing raw materials in water and heating the water-containing materials under pressure, and a wet method in which synthesis is carried out by heating water-containing raw materials at normal pressure, or the like.

Among these, the high-temperature heating synthesis method is carried out simply by preparing raw materials and heating the same at a high temperature, thus enabling synthesis of zirconium phosphate with an appropriately adjusted P/Zr ratio. However, with the high-temperature heating synthesis method, it is not easy to uniformly mix raw materials and it is difficult to obtain zirconium phosphate with a homogeneous composition. In addition, in order to convert agglomerate-form zirconium phosphate obtained by the high-temperature heating synthesis method into a powder zirconium phosphate, pulverization and screening are required, thus causing problems associated with quality and production efficiency. In addition, it is natural that, with the high-temperature heating synthesis method, it is impossible to synthesize crystalline zirconium phosphate containing ammonia. On the other hand, with a hydrothermal or wet method, it is possible to obtain zirconium phosphate with homogeneous particulates.

Ions such as silver, copper, zinc, tin, mercury, lead, iron, cobalt, nickel, manganese, arsenic, antimony, bismuth, barium, cadmium and chromium have been known for a long time as metal ions that exhibit antimold properties, antimicrobial properties and antialgal properties (hereinafter, referred to as "antimicrobial metal ions"). However, silver ions are widely used as an aqueous silver nitrate solution which exhibits disinfection or pasteurization actions. However, metal ions which exhibit antimold, antimicrobial or antialgal properties are often harmful to humans, thus there are various restrictions on an application method, a storage method, a disposal method and the like as well as limitations on the applications.

However, antimold properties, antimicrobial or antialgal properties can be obtained by applying a small amount of antimicrobial metals to subjects. As a result, as antimicrobial agents which exhibit antimold, antimicrobial or antialgal properties, organic support antimicrobial agents obtained by supporting antimicrobial metal ions on an ion exchange resin, a chelate resin or the like, and inorganic antimicrobial agents obtained by supporting antimicrobial metal ions on a clay mineral, an inorganic ion exchanger or a porous body have been suggested.

Among these, silver-based inorganic antimicrobial agents obtained by supporting silver ions on an inorganic compound have properties such as improved safety, long-lasting antimicrobial effects and superior heat resistance as compared to a silver nitrate aqueous solution, thus having few restrictions on an application method, a storage method, a disposal method and applications as well as currently being applied to a variety of products. However, silver ions are unstable when exposed to heat and light and are immediately reduced into silver metals, thus having a problem of stability such as discoloration over a long period of time. Depending on the type of inorganic compounds to support the silver ions, the performance of the obtained silver-based inorganic antimicrobial agents varies and the antimicrobial agents frequently have restrictions.

As a silver-based inorganic antimicrobial agent, an antimicrobial agent obtained by ion exchanging alkali metal ions such as sodium ions in clay minerals such as montmorillonites and zeolites, with silver ions, is known. Since the skeleton structure of a clay mineral has deteriorated acid resistance, for example, silver ions are readily eluted in an acidic solution and the antimicrobial effects cannot last for a long time.

In addition, there are silver-supports obtained by adding silver ions and ammonium ions to zeolites by ion exchange in order to impart stability to silver ions. However, in this case, the prevention of discoloration does not reach a practical level or provide a fundamental solution.

There are antimicrobial agents in which antimicrobial metals are supported on adsorbent active carbons. However, since these agents physically adsorb or adhere soluble antimicrobial metal salts, on contact with water, antimicrobial metal ions are rapidly eluted and the duration of the antimicrobial effects thereof is thus lost.

Recently, an antimicrobial agent obtained by supporting antimicrobial metal ions on a specific zirconium phosphate has been suggested. For example, PTL 4 discloses the following Formula (2).

$$M^1{}_a A_b M^2{}_c (PO_4)_d \cdot nH_2O \tag{2}$$

(In Formula 2, $M^1$ represents a metal ion selected from silver, copper, zinc, tin, mercury, lead, iron, cobalt, nickel, manganese, arsenic, antimony, bismuth, barium, cadmium and chromium, A represents at least one ion selected from an alkali metal ion, an alkaline earth metal ion, an ammonium ion and a hydrogen ion, $M^2$ represents a tetravalent metal, n represents a number satisfying $0 \leq n \leq 6$, a and b are positive numbers, c and d satisfy c=2 and d=3, provided that la+mb=1, and c and d satisfy c=1 and d=2, provided that la+mb=2, with the provisio that l is the valence of $M^1$ and m is the valence of A.)

Such an antimicrobial agent is known as a material which is chemically and physically stable and exerts antimold properties and antimicrobial properties for a long period of time. However, the elution rate of silver ions increases under specific environmental conditions, for example, in cases of applications requiring exposure to water for a long period of time and some antimicrobial products cannot thus exert long-lasting effects for a long period of time.

CITATION LIST

Patent Literature (PLT)

PTL 1: JP-A-6-48713 (JP-A denotes a Japanese unexamined patent publication application.)
PTL 2: JP-A-5-17112
PTL 3: JP-A-60-239313
PTL 4: JP-A-04-275370

Non-Patent Literature (NPL)

NPL 1: C. JAGER, et., al, "$^{31}$P and $^{29}$Si NMR Investigations of the Structure of NASICON-Strukturtyps", Expermentelle Technik der Physik, 1988, Vol. 36, No. 4/5, p 339-348
NPL 2: C. JAGER, et., al, "$^{31}$P MAS NMR STUDY OF THE NASICON SYSTEM $Na_{1+4y}Zr_{2-y}(PO_4)_3$", Chemical Physics Letters, 1988, Vol. 150, No. 6, p 503-505
NPL 3: H. Y—P. HONG, "CRYSTAL STRUCTURE AND CRYSTAL CHEMISTRY IN THE SYSTEM $Na_{1+x}Zr_2Si_xP_{3-x}O_{12}$", Mat. Res. Bull., Vol. 11, p. 173-182.

SUMMARY OF INVENTION

Problems to be Solved by the Invention

The present invention provides a silver-based inorganic antimicrobial agent and an antimicrobial product which exhibit superior heat resistance, chemical resistance and processability as well as superior long-lasting waterproofness.

Means for Solving the Problems

As a result of an intensive investigation to solve the problems, the present inventors discovered that the problems could be solved using the zirconium phosphate-based silver-based inorganic antimicrobial agent represented by Formula (1) containing zirconium pyrophosphate ($ZrP_2O_7$).

$$Ag_aM_bZr_cHf_d(PO_4)_3 \cdot nH_2O \quad (1)$$

(In Formula (1), M is at least one ion selected from an alkali metal ion, an ammonium ion, a hydrogen ion and an oxonium ion, a, b, c and d are positive numbers satisfying $1.75<(c+d)<2.2$, and $a+b+4(c+d)=9$, and n is 2 or less.)

Furthermore, the present invention is an antimicrobial product containing the silver-based inorganic antimicrobial product composed of the material.

Effects of the Invention

The silver-based inorganic antimicrobial agent of the present invention exhibits superior antimicrobial effects with long-lasting waterproofness, as compared to conventional silver-based zirconium phosphate antimicrobial agents.

DESCRIPTION OF SYMBOLS

Figure 1:
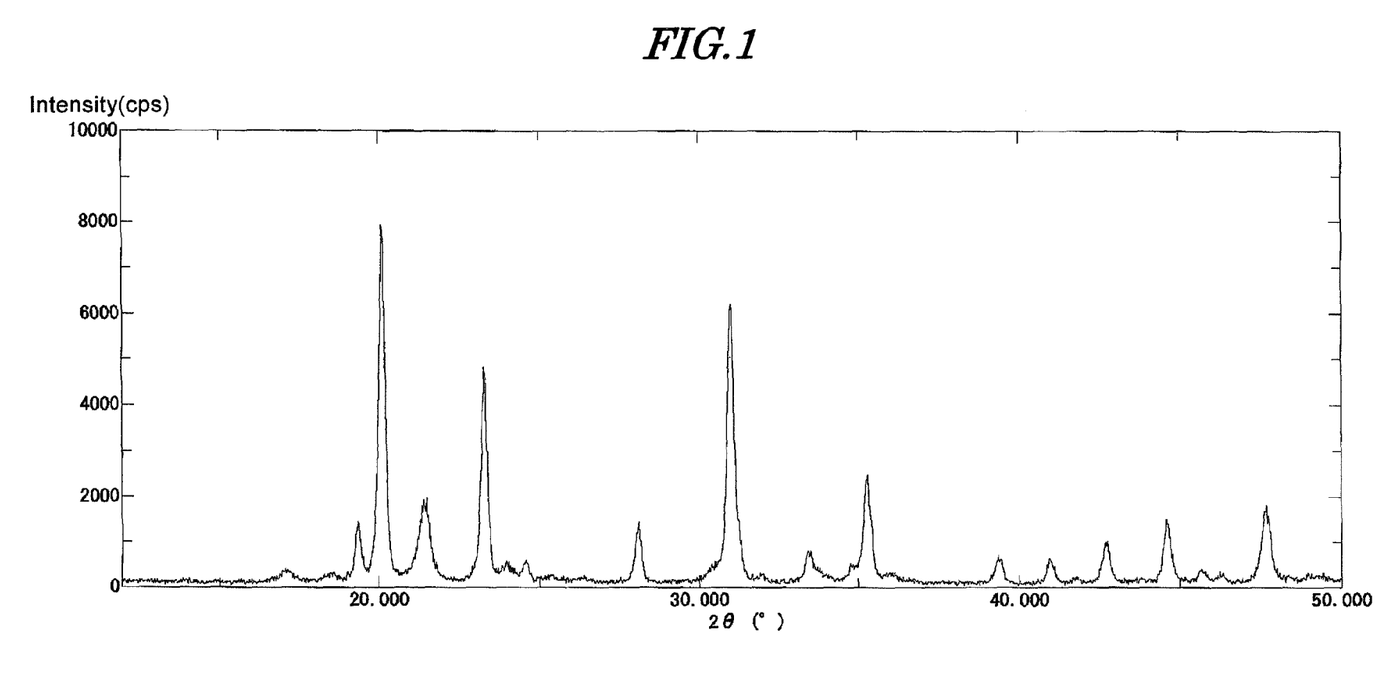
FIG. 1 is an X-ray diffraction pattern of an inorganic antimicrobial agent obtained in Example 1 measured by a powder X-ray diffraction apparatus.
Figure 2:
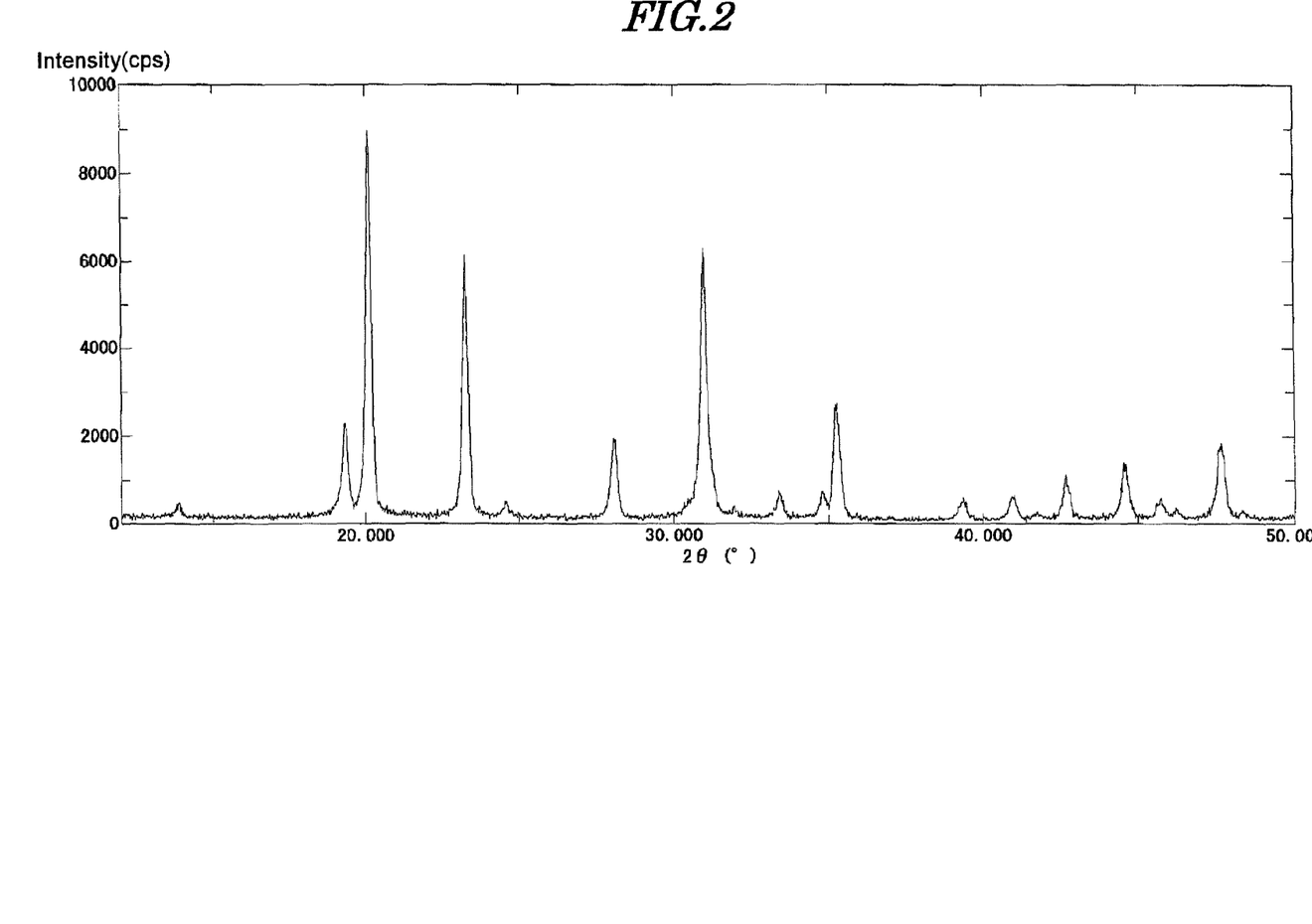
FIG. 2 is an X-ray diffraction pattern of an inorganic antimicrobial agent obtained in Comparative Example 4 measured by a powder X-ray diffraction apparatus.

In FIGS. 1 and 2, the vertical axis represents an X-ray intensity (unit: cps) during X-ray diffraction measurement.

In FIGS. 1 and 2, the horizontal axis represents a diffraction angle of an X-ray (unit: °).

DESCRIPTION OF EMBODIMENTS

Hereinafter, the present invention will be described. In addition, % means % by mass.

The inorganic antimicrobial agent of the present invention is an antimicrobial agent represented by Formula (1) containing zirconium pyrophosphate ($ZrP_2O_7$).

$$Ag_aM_bZr_cHf_d(PO_4)_3 \cdot nH_2O \quad (1)$$

(In Formula (1), M is at least one ion selected from an alkali metal ion, an ammonium ion, a hydrogen ion and an oxonium ion, a, b, c and d are positive numbers satisfying $1.75<(c+d)<2.2$, and $a+b+4(c+d)=9$, and n is 2 or less.)

In Formula (1), a satisfies 0<a and is preferably 0.01 or more, more preferably 0.03 or more, and a is preferably 1 or less, more preferably 0.6 or less. When a is lower than 0.01, there is a concern that antimicrobial properties are not sufficiently exerted.

An optimal value of b in Formula (1) varies depending on the type of M selected from an alkali metal ion, an ammonium ion, a hydrogen ion and an oxonium ion. b satisfies 0<b and is preferably 0.01 or more. In addition, b is lower than 1.5 and is preferably lower than 1.0, more preferably 0.9 or less. When b is large, the antimicrobial agent of the present invention may readily cause discoloration when mixed with a resin, and when b is 0.6 or more, discoloration may particularly readily occur.

In Formula (1), c and d satisfy $1.75<(c+d)<2.2$, c is preferably lower than 2.15, more preferably lower than 2.10, and is preferably 1.80 or more, more preferably 1.85 or more, yet more preferably 1.90 or more. In addition, d is preferably 0.2 or less, more preferably 0.001 to 0.15, yet more preferably 0.005 to 0.10.

A case where c+d is not greater than 1.75 or at least 2.2 is not preferable in that the uniform zirconium phosphate represented by Formula (1) cannot be readily obtained.

In Formula (1), n is preferably 1 or less, more preferably 0.01 to 0.5, particularly preferably 0.03 to 0.3. A case where n is higher than 2 is not preferable since the absolute amount of moisture contained in the silver-based inorganic antimicrobial agents of the present invention is high and there is a concern that foaming, hydrolysis or the like may occur during processing or the like, when mixed with a variety of materials.

Examples of the silver-based inorganic antimicrobial agents represented by Formula (1) may be provided as follows.

$Ag_{0.05}Na_{0.02}H_{0.3}(H_3O)_{0.55}Zr_{2.0}Hf_{0.02}(PO_4)_3 \cdot 0.15H_2O$ $Ag_{0.10}Na_{0.02}H_{0.32}(H_3O)_{0.40}Zr_{2.01}Hf_{0.03}(PO_4)_3 \cdot 0.10H_2O$ $Ag_{0.17}Na_{0.02}H_{0.65}Zr_{2.03}Hf_{0.01}(PO_4)_3 \cdot 0.05H_2O$ $Ag_{0.17}Na_{0.04}H_{0.2}(H_3O)_{0.55}Zr_{1.99}Hf_{0.02}(PO_4)_3 \cdot 0.25H_2O$ $Ag_{0.17}Na_{0.10}(H_3O)_{0.45}Zr_{1.92}Hf_{0.15}(PO_4)_3 \cdot 0.15H_2O$ $Ag_{0.17}Na_{0.12}K_{0.10}H_{0.2}(H_3O)_{0.25}Zr_{1.92}Hf_{0.05}(PO_4)_3 \cdot 0.15H_2O$ $Ag_{0.45}Na_{0.12}H_{0.55}Zr_{1.95}Hf_{0.02}(PO_4)_3 \cdot 0.05H_2O$ $Ag_{0.55}K_{0.1}H_{0.2}(H_3O)_{0.47}Zr_{1.99}Hf_{0.01}(PO_4)_3 \cdot 0.15H_2O$ $Ag_{0.17}Na_{0.20}K_{0.3}(H_3O)_{0.45}Zr_{1.92}Hf_{0.05}(PO_4)_3 \cdot 0.15H_2O$ $Ag_{0.45}Na_{0.12}H_{0.2}(H_3O)_{0.35}Zr_{1.95}Hf_{0.02}(PO_4)_3 \cdot 0.05H_2O$ $Ag_{0.55}Na_{0.1}H_{0.35}Zr_{1.99}Hf_{0.01}(PO_4)_3 \cdot 0.15H_2O$ The silver-based inorganic antimicrobial agent of the present invention is silver-based inorganic antimicrobial agent represented by Formula (1) containing zirconium pyrophosphate ($ZrP_2O_7$).

The zirconium pyrophosphate is integrated with the silver-based inorganic antimicrobial agent particles of Formula (1) and thus cannot be separated therefrom, and is not mixed with other compounds. Zirconium pyrophosphate cannot be separated from the silver-based inorganic antimicrobial agent and the content thereof can be confirmed from powder X-ray diffraction patterns. The powder X-ray diffraction pattern of zirconium pyrophosphate is ASTM File No. 29-1399, and values of d are 4.12(100), 3.69(40), 4.76(30), 3.37(30), 2.92 (30), 1.84(20), 1.59(20), 1.68(10). Meanwhile, the powder X-ray diffraction pattern of $AgZr_2(PO_4)_3$, a compound similar to the silver-based inorganic antimicrobial agent of Formula (1) is ASTM File No. 34-1245 and the values of d are 2.87(100), 4.38(50), 3.80(50), 2.67(50), 2.54(30), 1.90(30), 4.55(20) and 2.28(20).

In the powder X-ray diffraction pattern, the relative intensity of X-ray diffraction peaks at $2\theta=21.3°$ to $21.5°$ (the value of d corresponds to 4.1) indicating the presence of zirconium pyrophosphate crystals with respect to 100 of the X-ray diffraction peak intensity at $2\theta=20.0°$ to $20.2°$ (the value of d corresponds to 4.4) which indicates the crystal structure of silver-based inorganic antimicrobial agent represented by Formula (1) means the content of zirconium pyrophosphate crystals. When the relative intensity is excessively low, naturally, it is difficult to obtain an inhibition effect regarding the amount of eluted silver. Higher relative intensity is necessarily not better. There is an optimal relative intensity. A preferred relative intensity is 5 to 50, more preferably 10 to 40, particularly preferably 15 to 35. Hereinafter, the term "relative intensity of X-ray diffraction" means a relative intensity of X-ray diffraction peaks at $2\theta=21.3°$ to $21.5°$ (the value of d corresponds to 4.1) indicating the presence of zirconium pyrophosphate crystals, assuming that the X-ray diffraction peak intensity at $2\theta=20.0°$ to $20.2°$ (the value of d corresponds to 4.4) is 100.

As the absolute value of X-ray diffraction intensity measured with X-rays of 50 kV/120 mA at $2\theta=20.0°$ to $20.2°$ which indicates the crystal structure of silver-based inorganic antimicrobial agent represented by Formula (1) increases, superior crystallinity improves. In order to improve discoloration inhibition or durability of the silver-based inorganic antimicrobial agent, the absolute value is 4000 cps or higher, more preferably 5000 cps or more.

In addition, the silver-based inorganic antimicrobial agent represented by Formula (1) of the present invention is a silver-based inorganic antimicrobial agent obtained by performing ion exchange using an aqueous solution containing silver nitrate in an amount corresponding to the value obtained by multiplying 0.6 to 0.99 by b1, the coefficient of Formula 3, with respect to one mole of a zirconium phosphate compound represented by Formula 3 below, followed by thermal decomposition.

$$Na_{b1}A_{c1}Zr_eHf_f(PO_4)_3 \cdot nH_2O \quad (3)$$

(wherein A represents an ammonium ion and/or a hydrogen ion, and b1, c1, e and f are positive numbers satisfying $1.75<(e+f)<2.25$, and $b1+c1+4(e+f)=9$)

A method for synthesizing zirconium phosphate represented by Formula (3) is preferably a wet method or a hydrothermal method in which a variety of raw materials are reacted in an aqueous solution. Specifically, the synthesis of zirconium phosphate of Formula (3) wherein A represents an ammonium ion may be carried out by adjusting an aqueous solution containing predetermined amounts of zirconium compound, ammonia or a salt thereof, oxalic acid or a salt thereof, and phosphoric acid or a salt thereof, to pH 4 or less with sodium hydroxide or ammonia water, and heating the solution to 70° C. or higher.

Specifically, the synthesis of zirconium phosphate of Formula (3) wherein A represents a hydrogen ion may be carried out by adjusting an aqueous solution containing predetermined amounts of zirconium compound, oxalic acid or a salt thereof, and phosphoric acid or a salt thereof, to pH 4 or less with sodium hydroxide and heating the solution at a temperature of 70° C. or higher, and stirring the resulting zirconium phosphate in an aqueous solution such as hydrochloric acid, acetic acid or sulfuric acid to support a hydrogen ion. In addition, the supporting of hydrogen ions may be performed simultaneously with supporting of silver ions using silver nitrate or after the supporting of silver ions. The synthesized zirconium phosphate is further separated by filtration, washed with water until an electrical conductivity reaches a predetermined level, dried and slightly ground to obtain white particulate zirconium phosphate. In addition, a hydrothermal method in which synthesis is performed at a temperature higher than 100° C. under pressure enables synthesis of zirconium phosphate represented by Formula (3) without using oxalic acid or a salt thereof.

The zirconium compound that can be used as a raw material for synthesizing zirconium phosphate represented by Formula (3) may be a water-soluble or acid-soluble zirconium salt. Examples of the zirconium compound include zirconium nitrate, zirconium acetate, zirconium sulfate, basic zirconium sulfate, zirconium oxysulfate, and zirconium oxychloride and zirconium oxychloride is preferred in view of reactivity, economic efficiency and the like.

The hafnium compound that can be used as a raw material for synthesizing zirconium phosphate represented by Formula (3) may be a water-soluble or acid-soluble hafnium salt, examples thereof include hafnium chloride, hafnium oxychloride, hafnium ethoxide and the like and the hafnium compound may be zirconium compound containing hafnium. The content of hafnium present in the zirconium compound is preferably 0.1% to 5%, more preferably 0.3% to 4%. In the present invention, use of zirconium oxychloride containing a small amount of such hafnium is preferred in view of reactivity, economic efficiency or the like.

Examples of oxalic acid or a salt thereof that can be used as a raw material for synthesizing zirconium phosphate represented by Formula (3) include oxalic acid dihydrate, sodium oxalate, ammonium oxalate, sodium hydrogen oxalate, and ammonium hydrogen oxalate and oxalic acid dihydrate is preferred.

Examples of ammonia or a salt thereof that that can be used as a raw material for synthesizing zirconium phosphate represented by Formula (3) include ammonium chloride, ammonium nitrate, ammonium sulfate, aqueous ammonia, ammonium oxalate, and ammonium phosphate, and ammonium chloride or aqueous ammonia are preferred.

The phosphoric acid or a salt thereof that can be used as a raw material for synthesizing zirconium phosphate represented by Formula (3) is preferably a soluble or acid-soluble salt and specific examples thereof include phosphoric acid, sodium phosphate, sodium hydrogen phosphate, ammonium hydrogen phosphate and ammonium phosphate, and phosphoric acid is more preferred. The concentration of the phosphoric acid is preferably about 60% to about 85%.

The molar ratio of phosphoric acid or a salt thereof to the zirconium compound (assuming that the zirconium compound is 1) when synthesizing a zirconium phosphate represented by Formula (3) is preferably higher than 1.5 and lower than 2, more preferably not less than 1.51 and lower than 1.71, yet more preferably 1.52 to 1.67, particularly preferably 1.52 to 1.65.

That is, the zirconium phosphate represented by Formula (3) can be preferably synthesized by a wet or hydrothermal method in which the number of moles of phosphoric acid or a salt thereof per mole of zirconium compound is higher than 1.5 and lower than 2.

In addition, the molar ratio of phosphoric acid or a salt thereof to ammonia or a salt thereof (assuming that the ammonia or a salt thereof is 1) when synthesizing a zirconium phosphate represented by Formula (3) is preferably 0.3 to 10, more preferably 1 to 10, particularly preferably 2 to 5.

The molar ratio of phosphoric acid or a salt thereof to oxalic acid or a salt thereof (assuming that the oxalic acid or a salt thereof is 1) when synthesizing a zirconium phosphate represented by Formula (3) is preferably 1 to 6, more preferably 1.5 to 5, yet more preferably 1.51 to 4, particularly preferably 1.52 to 3.5.

That is, the zirconium phosphate represented by Formula (3) can be preferably synthesized by a wet method using oxalic acid or a salt thereof or a hydrothermal method. The hydrothermal method does not require of the inclusion oxalic acid or a salt thereof.

The concentration of solid present in the reaction slurry when synthesizing a zirconium phosphate represented by Formula (3) is preferably 3% by mass or more, more preferably 7% to 20% in view of efficiency such as economic efficiency.

When synthesizing a zirconium phosphate represented by Formula (3), the pH is preferably 1 to 4, more preferably 1.3 to 3.5, yet more preferably 1.8 to 3.0, particularly preferably 2.0 to 3.0. When the pH exceeds 4, it is not preferred in that zirconium phosphate represented by Formula (3) cannot always be synthesized. When the pH is lower than 1, it is not preferred in that zirconium phosphate represented by Formula (3) cannot always be synthesized. For adjustment of the pH, it is preferable to use sodium hydroxide, potassium hydroxide, aqueous ammonia, etc., and it is more preferable to use sodium hydroxide.

The synthesis temperature when synthesizing a zirconium phosphate represented by Formula (3) is preferably 70° C. or more, more preferably 80° C. or more, yet more preferably 90° C. or more, particularly preferably 95° C. or more. In addition, the synthesis temperature is preferably 150° C. or less, more preferably 120° C. or less. When the temperature is lower than 70° C., it is not preferred in that zirconium phosphate represented by Formula (3) cannot always be synthesized. In addition, when the temperature exceeds 150° C., it is not preferred due to a disadvantage in terms of energy.

When synthesizing zirconium phosphate represented by Formula (3), stirring is preferably performed so that raw materials can be uniformly mixed and the reaction is uniformly performed.

The synthesis time of zirconium phosphate represented by Formula (3) depends on the synthesis temperature. For example, the synthesis time of zirconium phosphate of the present invention is preferably 4 hours or longer, more preferably 8 hours to 72 hours, yet more preferably 10 hours to 48 hours.

In the zirconium phosphate represented by Formula (3), zirconium phosphate having a median diameter of 0.1 to 5 μm can be synthesized. The median diameter of zirconium phosphate represented by Formula (3) is preferably 0.1 to 4 μm, more preferably 0.2 to 3 μm, yet more preferably 0.3 to 2 μm. In addition, in view of processability into a variety of products, a maximum particle size as well as the median diameter is important. In this regard, the maximum particle size of zirconium phosphate represented by Formula (3) is preferably 10 μm or less, more preferably 6 μm or less, particularly preferably 4 μm or less.

Specific examples of zirconium phosphate represented by Formula (3) that can be used as a raw material of the silver-based inorganic antimicrobial agent are provided as follows:

$Na_{0.07}(NH_4)_{0.85}Zr_{2.0}Hf_{0.02}(PO_4)_3 \cdot 0.65H_2O$
$Na_{0.12}(NH_4)_{0.65}Zr_{2.01}Hf_{0.03}(PO_4)_3 \cdot 0.85H_2O$
$Na_{0.19}(NH_4)_{0.65}Zr_{2.03}Hf_{0.01}(PO_4)_3 \cdot 0.75H_2O$
$Na_{0.21}(NH_4)_{0.75}Zr_{1.99}Hf_{0.02}(PO_4)_3 \cdot 0.6H_2O$
$Na_{0.27}(NH_4)_{0.75}Zr_{1.92}Hf_{0.15}(PO_4)_3 \cdot 0.75H_2O$
$Na_{0.29}(NH_4)_{0.55}Zr_{1.92}Hf_{0.05}(PO_4)_3 \cdot 0.5H_2O$
$Na_{0.57}(NH_4)_{0.55}Zr_{1.95}Hf_{0.02}(PO_4)_3 \cdot 0.35H_2O$
$Na_{0.70}(NH_4)_{0.85}Zr_{1.99}Hf_{0.01}(PO_4)_3 \cdot 0.4H_2O$
$Na_{0.07}H_{0.35}Zr_{2.0}Hf_{0.02}(PO_4)_3 \cdot 0.65H_2O$
$Na_{0.12}H_{0.65}Zr_{2.01}Hf_{0.03}(PO_4)_3 \cdot 0.85H_2O$
$Na_{0.19}H_{0.65}Zr_{2.03}Hf_{0.01}(PO_4)_3 \cdot 0.75H_2O$
$Na_{0.21}H_{0.75}Zr_{1.99}Hf_{0.02}(PO_4)_3 \cdot 0.6H_2O$
$Na_{0.27}H_{0.75}Zr_{1.92}Hf_{0.15}(PO_4)_3 \cdot 0.75H_2O$
$Na_{0.29}H_{0.55}Zn_{0.92}Hf_{0.05}(PO_4)_3 \cdot 0.5H_2O$
$Na_{0.57}H_{0.55}Zr_{1.95}Hf_{0.02}(PO_4)_3 \cdot 0.35H_2O$
$Na_{0.70}H_{0.85}Zr_{1.99}Hf_{0.1}(PO_4)_3 \cdot 0.4H_2O$ In order to obtain the silver-based inorganic antimicrobial agent of Formula (1), zirconium phosphate thereof is subjected to silver-ion exchange and then thermal decomposition. A silver-ion exchange method is to dip zirconium phosphate in a silver nitrate-containing aqueous solution. The content of silver nitrate in the aqueous solution is preferably as large as possible, since discoloration can be inhibited when the obtained silver-based inorganic antimicrobial agent is mixed with a resin. A case where silver nitrate is present in an excessively large amount is not economically preferable since excess silver ions remain in the aqueous solution. The use of an aqueous solution containing silver nitrate in an amount corresponding to the value obtained by multiplying 0.6 to 0.99 by b1, the coefficient of Formula 3 is preferable, and the use of an aqueous solution containing silver nitrate in an amount corresponding to the value obtained by multiplying 0.7 to 0.98 by b1, the coefficient of Formula 3, with respect to one mole of a zirconium phosphate compound represented by Formula 3, is more preferable. The amount of zirconium phosphate in the aqueous solution may be determined such that the zirconium phosphate can be uniformly mixed with the aqueous solution. Specifically, the amount of the zirconium phosphate represented by Formula (3) is 20% by weight or less, based on the total amount of the aqueous solution.

The adjustment of the aqueous solution containing silver ions preferably uses an aqueous solution in which silver nitrate is dissolved in deionized water. The temperature of the aqueous solution during ion exchange may be 0 to 100° C., preferably, 20 to 80° C. Since this ion exchange is rapidly performed, a dipping time may be 5 minutes or less, and is preferably 30 minutes to 5 hours in order to obtain a uniform and high silver-ion exchange ratio. Even if the dipping is performed for 5 hours or more, the silver ions are not exchanged further.

After completion of the silver-ion exchange, the resulting product is preferably washed with deionized water. After washing, the resulting product is filtered, dried and thermally decomposed in a state where the bulk specific gravity thereof is adjusted to a suitable level, to obtain a silver-based inorganic antimicrobial agent represented by Formula (1) containing a predetermined concentration of zirconium pyrophosphate.

The washing with water is preferably performed until a suitable washing degree can be obtained, and the term "suitable washing degree" means that the electrical conductivity of the aqueous particle suspension is 15 µS to 570 µS, and more preferably is 20 µS to 470 µS, when the particles are suspended in deionized water. In addition, S, the unit of electrical conductivity is defined as an inverse number of ohm, the unit of electrical conductivity, which is a SI-derived unit called "siemens".

After washing with water, the silver-based inorganic antimicrobial agent is separated as a solid by filtration and dried temporarily. The filtration-separated and dried substance is present as a large agglomerate, but an inner calcination thereof is insufficient and qualities thereof may be readily deteriorated due to low thermal conductance when calcined. Accordingly, the dried solid is preferably ground into a lump having a predetermined size. The pulverization may be performed by hand, or by colliding large lumps when the solid is hard, or beating using a hammer or the like. This pulverization may be carried out using a pulverization apparatus such as a ball mill, a hammer mill, a pin mill or a Raikai grinding machine. In order to obtain silver-based inorganic antimicrobial agents which enable zirconium pyrophosphate and zirconium phosphate to coexist and exhibit an antimicrobial property, elution property and the like, it is necessary to thermally decompose a pulverized and slightly aggregated powder. When the powder is excessively pulverized, there is a concern that sintering severely occurs and pulverization is difficult after thermal decomposition.

The filtration-separated and dried solid is aggregated and thus has a bulk specific gravity, but becomes a fine powder and thus has a decreased bulk specific gravity when pulverized. Accordingly, bulk specific gravity may be used as a parameter to define a suitable pulverization degree. In the present invention, the bulk specific gravity may be determined by statically filling a powder in a container or beaker having a volume of 1 L, scraping a peak top part using a paddle and measuring a total weight, based on substantially the same concept as an apparent density (bulk specific gravity) by a static method defined in for example JIS K5101-1991. In the preparation of the inorganic antimicrobial agent of the present invention, the bulk specific gravity of powder before thermal decomposition is preferably 0.80 to 2.00 (g/ml), more preferably 0.90 to 1.45 (g/ml), yet more preferably 1.00 to 1.35 (g/ml).

The thermal decomposition may be carried out at 800° C. to 1,100° C., preferably 820° C. to 1050° C., more preferably, 850° C. to 950° C. The thermal decomposition temperature is preferably 800° C. or more from a viewpoint of obtaining sufficient inhibition effects of silver elution, and is preferably 1,000° C. or less from a viewpoint of avoiding aggregation of particles by dissolution. The thermal decomposition may be carried out using an electric furnace, a gas furnace or the like. Particles may be added to a flame retardant box or directly placed in a furnace, and stirring may be performed while heating. A thermal decomposition temperature strictly means a particle surface temperature, and may be measured using a thermometer which protrudes near the particle surface in the furnace, an emission pyrometer or the like. As an industrial method, a gas furnace is commonly used, and a method in which particles placed in the flame-retardant box are stacked by opening an aperture and hot air heated by a combustion gas is circulated in a furnace may be used.

The amount of silver eluted from the silver-based inorganic antimicrobial agent of the present invention can be controlled by thermal decomposition. That is, the antimicrobial agent before thermal decomposition exhibits a rapid decrease in elution amount over time due to an excessively high amount of eluted silver; the antimicrobial agent after thermal decomposition exhibits a reduced concentration decrease over time due to inhibition of the decomposition of the initial amount of eluted silver. The amount of eluted silver before thermal decomposition is preferably 10% to 70% of the amount of eluted silver after thermal decomposition.

When a time at which thermal decomposition is performed is long, discoloration resistance improves and uniform properties can be obtained, but when the time is excessively long, economic efficiency cannot be obtained. Accordingly, the thermal decomposition time is preferably one hour or more, and is preferably 2 hours to 60 hours from a viewpoint of improvement of discoloration resistance, more preferably, 4 hours to 36 hours. In addition, since the relation between the temperature and thermal decomposition time is important, thermal decomposition is possible for 6 hours to 60 hours when the temperature is 850° C., for 2 hours to 48 hours when the temperature is 900° C., and for one hour to 36 hours when the temperature is 950° C.

After thermal decomposition, particles of silver-based inorganic antimicrobial agent of the present invention may be aggregated. Therefore, the aggregated particles are preferably pulverized using a grinding apparatus.

The form in which the silver-based inorganic antimicrobial agent is used is not particularly limited and may be suitably mixed with other constituents or combined with other materials depending on the application. Examples of the form include a variety of forms including powders, powder-containing dispersions, powder-containing particles, powder-containing coatings, powder-containing fibers, powder-containing papers, powder-containing plastics, powder-containing films, powder-containing aerosols and the like. If necessary, the antimicrobial agent may be used in combination with a variety of additives or materials such as other antimicrobial agents, deodorants, antiviral agents, anti-allergic agents, photocatalysts, flame retardants, anticorrosion agents, fertilizers, construction materials and the like.

The silver-based inorganic antimicrobial agent of the present invention may be mixed with a variety of additives to improve kneading processability or other physical properties of resins. Specific examples thereof include pigments such as zinc oxide or titanium oxide, inorganic ion exchangers such as zirconium phosphates or zeolites, dyes, antioxidants, light resistance stabilizers, flame retardants, antistatic agents, defoaming agents, impact resistance reinforcing agents, glass fibers, lubricants such as metal soaps, moisture resistance agents and extenders, coupling agents, nucleating agents, flow modifiers, deodorants, wood powders, antifungal agents, antifouling agents, anticorrosion agents, metal powders, UV absorbers, UV blockers and the like.

An antimicrobial resin composition can be easily obtained by mixing the silver-based inorganic antimicrobial agent of the present invention with a resin. The type of the resin that can be used is not particularly limited and may be any of a natural resin, a semi-synthetic resin, and a synthetic resin, and may be either a thermoplastic resin or a thermosetting resin. Specifically, the resin may be any one of a molding resin, a fiber resin, and a rubber resin, and examples of the resin include molding or fiber resins such as polyethylene, polypropylene, vinyl chloride, ABS resins, AS resins, MBS resins, nylon resins, polyester, polyvinylidene chloride, polystyrene, polyacetal, polycarbonate, PBT, acrylic resins, fluorine resins, polyurethane elastomers, polyester elastomers, melamine resins, urea resins, ethylene tetrafluoride resins, unsaturated polyester resins, rayon, acetate, acrylic, polyvinyl alcohol, cupro, triacetate, and vinylidene; and rubber resins such as natural rubbers, silicone rubbers, styrene butadiene rubbers, ethylene propylene rubbers, fluorine rubbers, nitrile rubbers, chlorosulfonated polyethylene rubbers, butadiene rubbers, synthetic natural rubbers, butyl rubbers, urethane rubbers, and acrylic rubbers. In addition, antimicrobial fibers may be prepared by combining the silver-based inorganic antimicrobial agent of the present invention with fibers such as natural fibers.

A mixing ratio of the silver-based inorganic antimicrobial agent of the present invention in the antimicrobial resin composition is preferably 0.1 to 50 parts by weight and is more preferably 0.3 to 20 parts by weight with respect to 100 parts by weight of the antimicrobial resin composition. When the proportion is lower than 0.1 parts by weight, the improvement in the long-lasting antimicrobial property of the antimicrobial resin composition may be insufficient. Meanwhile, even when the proportion is higher than 50 parts by weight, antimicrobial effects are not significantly improved and economic efficiency may be decreased and the physical properties of resins may be considerably deteriorated.

A method for obtaining resin molded articles by mixing the silver-based inorganic antimicrobial agent of the present invention with a resin may be any one selected from methods known in the art. Examples of the method include (1) directly mixing a pellet-shaped resin or powder-type resin using an adhesive to facilitate adhesion of a silver-based inorganic antimicrobial agent powder to a resin, or a dispersant to improve dispersibility of the antimicrobial agent powder with a mixer, (2) molding the mixed composition thus obtained into pellets using an extrusion molding machine and mixing the molded material with another pellet-type resin, (3) molding the silver-based inorganic antimicrobial agent into pellets with a high concentration using a wax and mixing the pellet-shaped molded materials with another pellet-type resin, (4) dispersing the silver-based inorganic antimicrobial agent in a highly viscous liquid such as a polyol, followed by mixing, to prepare a paste-type composition and mixing the paste with a pellet-type resin and the like.

The molding of the antimicrobial resin composition may be carried out using any known processing techniques and machines depending on the characteristics of a variety of resins, the composition may be easily prepared in accordance with a mixing, incorporation or kneading method while heating and pressurizing or depressurizing at a suitable temperature or pressure, and the detailed operation thereof may be carried out using a common method and the composition may be molded into a variety of forms such as a lump, sponge, film, sheet, filament or pipe form or a combination thereof. The articles of the composition can exert antimicrobial property through use in combination with the silver-based inorganic antimicrobial agent of the present invention and are thus called "antimicrobial products".

The use form of the silver-based inorganic antimicrobial agent of the present invention is not particularly limited and is not limited to mixing with resin molded articles or polymer compounds. The antimicrobial agent may be mixed with other component or combined with other materials, depending on whether the application requires antifungal properties, antialgal properties or antimicrobial properties. For example, the antimicrobial agent may be used in a variety of forms such as powder, powder dispersion, particulate, aerosol or liquid forms. All of them fall within the scope of antimicrobial products.

The silver-based inorganic antimicrobial agent of the present invention also exhibits superior long-lasting waterproofness and is thus effectively utilized in applications associated with water contact. Examples thereof include washable textile products, pipes or tanks through which water passes or in which water is contained, kitchen appliances in contact with water, toiletry products, sponges and the like. All of these products also fall within the scope of antimicrobial products.

Applications of Antimicrobial Products

The silver-based inorganic antimicrobial agent of the present invention may be utilized in a variety of fields requiring antimold, antialgal and antimicrobial properties, such as electrical products, kitchen products, fiber products, house construction material products, bathroom products, paper products, toys, leather products, stationery and other products and the like.

More specifically, examples of the application include electrical products including dishwashers, dish dryers, refrigerators, washing machines, pots, televisions, PCs, radio cassette players, cameras, video cameras, water purifiers, rice cookers, vegetable cutters, registers, blanket dryers, FAXs, extractor fans, air conditioners and the like, and kitchen products including dishes, cutting boards, guillotines, trays, chopsticks, tea supply machines, thermos bottles, kitchen knives, ladle handles, fried egg turners, lunchboxes, paddles, bowls, draining racks, triangular food waste baskets, scrubbing brush containers, waste baskets, draining bags and the like.

The fiber products include shower curtains, cotton futons, air conditioner filters, pantyhose, socks, wet towels, sheets, blanket covers, pillows, gloves, aprons, curtains, diapers, bandages, masks, sports wear and the like. The house construction material products include decorative laminates, wallpapers, floorboards, window films, knobs, carpets, mats, artificial marbles, balustrades, masonry joints, tiles, waxes and the like. In addition, bathroom products include toilet seats, bathtubs, tiles, chamber pots, diaper boxes, toilet brushes, bathtub covers, pumice stones, soap cases, bathroom chairs, garment baskets, showers, basins and the like. Paper products include wrapping paper, pill paper, drug boxes, sketch books, medical charts, notes, paper for folding and the like. The toys include dolls, stuffed toys, paper clays, blocks, puzzles and the like.

In addition, leather products include shoes, bags, belts, watch bands or the like, indoor parts, chairs, globes, straps and the like. Stationery includes ballpoint pens, mechanical pencils, pencils, erasers, crayons, paper, notebooks, flexible disks, rulers, sticky notes such as Post it (trade name), staplers and the like.

Other products include insoles, make-up cases, scrubbing brushes, make-up puffs, hearing aids, musical instruments, cigarette filters, sticky sheets for cleaning, strap grips, sponges, kitchen towels, cards, microphones, hairdressing products, vending machines, shavers, telephones, thermometers, stethoscopes, slippers, garment cases, tooth brushes, sand in sandpits, food package films, antimicrobial sprays, coatings and the like.

EXAMPLES

Hereinafter, the present invention will be described with reference to examples and is not limited thereto.

Unless specifically otherwise mentioned, % means % by mass. The median particle size was analyzed on a volume basis using a laser diffraction particle size distribution meter.

The amount of zirconium was calculated by dissolving a sample using a strong acid and subjecting this liquid to measurement with an ICP emission spectrophotometer. The amount of phosphorus was calculated by first dissolving a sample using a strong acid and subjecting this liquid to measurement with an ICP emission spectrophotometer. The amount of sodium was calculated by dissolving a sample using a strong acid and subjecting this liquid to measurement with an atomic absorption spectrometer. The amount of ammonia was calculated by dissolving a sample using a strong acid and subjecting this liquid to measurement by an indophenol method. The amount of oxonium ions was calculated by measuring an amount of decreased mass at 160 to 190° C. through thermal analysis. The powder X-ray diffraction intensity means an X-ray diffraction intensity (unit: cps) at a specific reflection angle measured with CuKα rays of 50 kV/120 mA using a powder X-ray diffraction analyzer. A minimal growth inhibition concentration (MIC, μg/ml) to $E.$ $coli$ was obtained by pour-culturing samples at concentrations of 1000, 500, 250, 125 and 62.5 μg/ml on a heated and fused normal agar medium, inoculating $E.$ $coli$ on the solidified plate and measuring a minimal concentration, showing no proliferation. An amount of eluted silver was obtained by adding 0.1% of an organic antimicrobial agent, with respect to the total amount, to a 0.1% aqueous sodium nitrate solution, followed by shaking at 25° C. for one hour, and measuring a concentration of silver eluted in the filtrate of the resulting aqueous solution using an ICP emission spectrophotometer.

Example 1

0.1 moles of oxalic acid dihydrate, 0.2 moles of zirconium oxychloride octahydrate containing 0.17% of hafnium, and 0.05 moles of ammonium chloride were dissolved in 300 mL of deionized water, and 0.3 moles of phosphoric acid were added thereto while stirring. The pH of this solution was adjusted to 2.6 using a 20% aqueous sodium hydroxide solution, and the solution was then stirred at 98° C. for 14 hours. Subsequently, the precipitate thus obtained was washed well and dried at 120° C. to synthesize a zirconium phosphate compound.

Respective component amounts of this zirconium phosphate compound were measured and a composition formula thereof was obtained as follows:

$Na_{0.6}(NH_4)_{0.4}Zr_{1.98}Hf_{0.02}(PO_4)_3 \cdot 0.09H_2O$ 450 ml of an aqueous solution of deionized water obtained by dissolving 0.05 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 220 μS, and the resulting solid was dried at 120° C. and bulk specific gravity thereof was adjusted to 1.21.

Respective components of the dried solid composed of the silver-supported zirconium phosphate were measured and the resulting composition formula was given as follows:

$Ag_{0.55}Na_{0.05}H_{0.55}Zr_{1.98}Hf_{0.02}(PO_4)_3 \cdot 0.13H_2O$

In addition, the dried product was treated using a gas furnace at 900° C. for 12 hours to perform thermal decomposition. After thermal decomposition, the powder X-ray diffraction pattern of the silver-supporting zirconium phosphate was measured. As a result, the relative intensity at a peak of 2θ=21.4, indicating zirconium pyrophosphate, with respect to the X-ray intensity at 2θ=20.1, indicating the zirconium phosphate compound, was 22. This powder was pulverized to obtain a silver-based inorganic antimicrobial agent of the present invention.

The median diameter (μm), maximum particle size (μm), minimum concentration of growth inhibition to $E.$ $coli$ (MIC, μg/ml), and concentration of eluted silver (ppm) of the silver-based antimicrobial agent were measured and the results thus obtained are shown in Table 1.

Example 2

A silver-supporting process using the zirconium phosphate having the following composition formula obtained in Example 1 was changed as follows.

$Na_{0.6}(NH_4)_{0.4}Zr_{1.98}Hf_{0.02}(PO_4)_3 \cdot 0.09H_2O$ 450 ml of an aqueous solution of deionized water obtained by dissolving 0.05 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 380 μS, and the resulting solid was dried at 120° C. and bulk specific gravity thereof was adjusted to 1.00.

Respective components of the dried solid composed of the silver-supported zirconium phosphate were measured and the resulting composition formula was given as follows:

$Ag_{0.55}Na_{0.05}H_{0.55}Zr_{1.98}Hf_{0.02}(PO_4)_3 \cdot 0.14H_2O$

Furthermore, the dried product was treated using a gas furnace at 900° C. for 9 hours to perform thermal decomposition. After thermal decomposition, the powder X-ray diffraction pattern of the silver-supporting zirconium phosphate was measured. As a result, the relative intensity at a peak of 2θ=21.4, indicating zirconium pyrophosphate, with respect to the X-ray intensity at 2θ=20.1, indicating the zirconium phosphate compound, was 18. This powder was pulverized to obtain a silver-based inorganic antimicrobial agent of the present invention.

The median diameter (μm), maximum particle size (μm), minimum concentration of growth inhibition to $E.$ $coli$ (MIC, μg/ml), and concentration of eluted silver (ppm) of the silver-based antimicrobial agent were measured and the results thus obtained are shown in Table 1.

Example 3

A silver-supporting process using the zirconium phosphate having the following composition formula obtained in Example 1 was changed as follows.

$Na_{0.6}(NH_4)_{0.4}Zr_{1.98}Hf_{0.02}(PO_4)_3 \cdot 0.09H_2O$ 450 ml of an aqueous solution of deionized water obtained by dissolving 0.05 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 240 μS, and the resulting solid was dried at 120° C. and bulk specific gravity thereof was adjusted to 1.25.

Respective components of the dried solid composed of the silver-supported zirconium phosphate were measured and the resulting composition formula was given as follows:

$$Ag_{0.55}Na_{0.35}H_{0.25}Zr_{1.98}Hf_{0.02}(PO_4)_3 \cdot 0.11H_2O$$

Then, the dried product was treated using a gas furnace at 800° C. for 24 hours to perform thermal decomposition. After thermal decomposition, the powder X-ray diffraction pattern of the silver-supporting zirconium phosphate was measured. As a result, the relative intensity at a peak of 2θ=21.4, indicating zirconium pyrophosphate, with respect to the X-ray intensity at 2θ=20.1, indicating the zirconium phosphate compound, was 8. This powder was pulverized to obtain a silver-based inorganic antimicrobial agent of the present invention.

The median diameter (μm), maximum particle size (μm), and minimum concentration of growth inhibition to *E. coli* (MIC, μg/ml) of the silver-based antimicrobial agent were measured and the results thus obtained are shown in Table 1.

Example 4

0.1 moles of oxalic acid dihydrate, 0.2 moles of zirconium oxychloride octahydrate containing 0.17% of hafnium, and 0.3 moles of ammonium chloride were dissolved in 300 mL of deionized water, and 0.3 moles of phosphoric acid were added thereto while stirring. The pH of this solution was adjusted to 2.6 using a 20% aqueous sodium hydroxide solution, and the solution was then stirred at 98° C. for 8 hours. Subsequently, the precipitate thus obtained was washed well and dried at 120° C. to synthesize a zirconium phosphate compound.

Respective component amounts of this zirconium phosphate compound were measured and a composition formula thereof was obtained as follows:

$$Na_{1.0}Zr_{1.98}Hf_{0.02}(PO_4)_3 \cdot 0.09H_2O$$

450 ml of an 1N aqueous nitric acid solution obtained by dissolving 0.05 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 220 μS, and the resulting solid was dried at 120° C. and bulk specific gravity thereof was adjusted to 1.21.

Respective components of the dried solid composed of the silver-supported zirconium phosphate were measured and the resulting composition formula was given as follows:

$$Ag_{0.55}Na_{0.25}H_{0.35}Zr_{1.98}Hf_{0.02}(PO_4)_3 \cdot 0.11H_2O$$

Furthermore, the dried product was treated using a gas furnace at 900° C. for 12 hours to perform thermal decomposition. After thermal decomposition, the powder X-ray diffraction pattern of the silver-supporting zirconium phosphate was measured. As a result, the relative intensity at a peak of 2θ=21.4, indicating zirconium pyrophosphate, with respect to the X-ray intensity at 2θ=20.1, indicating the zirconium phosphate compound, was 22. This powder was pulverized to obtain a silver-based inorganic antimicrobial agent of the present invention.

The median diameter (μm), maximum particle size (μm), minimum concentration of growth inhibition to *E. coli* (MIC, μg/ml), and concentration of eluted silver (ppm) of the silver-based antimicrobial agent were measured and the results thus obtained are shown in Table 1.

Example 5

0.1 moles of oxalic acid dihydrate, 0.2 moles of zirconium oxychloride octahydrate containing 0.15% of hafnium and 0.02 moles of ammonium chloride were dissolved in 300 mL of deionized water, and 0.3 moles of phosphoric acid were added thereto while stirring. The pH of this solution was adjusted to 2.6 using a 20% aqueous sodium hydroxide solution, and the solution was then stirred at 98° C. for 6 hours. Subsequently, the precipitate thus obtained was washed well and dried at 120° C. to synthesize a zirconium phosphate compound.

Respective component amounts of this zirconium phosphate compound were measured and a composition formula thereof was obtained as follows:

$$Na_{0.80}K_{0.20}Zr_{1.98}Hf_{3.02}(PO_4)_3 \cdot 0.11H_2O$$

450 ml of an aqueous solution of deionized water obtained by dissolving 0.05 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 210 μS, and the resulting solid was dried at 120° C. and bulk specific gravity thereof was adjusted to 1.16.

Respective components of the dried solid composed of the silver-supported zirconium phosphate were measured and the resulting composition formula was given as follows:

$$Ag_{0.55}Na_{0.15}K_{0.19}H_{0.11}Zr_{1.98}Hf_{0.02}(PO_4)_3$$

Furthermore, the dried product was treated using a gas furnace at 850° C. for 24 hours to perform thermal decomposition. After thermal decomposition, the powder X-ray diffraction pattern of the silver-supporting zirconium phosphate was measured. As a result, the relative intensity at a peak of 2θ=21.4, indicating zirconium pyrophosphate, with respect to the X-ray intensity at 2θ=20.1, indicating the zirconium phosphate compound, was 22. This powder was pulverized to obtain a silver-based inorganic antimicrobial agent of the present invention.

The median diameter (μm), maximum particle size (μm), and minimum concentration of growth inhibition to *E. coli* (MIC, μg/ml) of the silver-based antimicrobial agent were measured and the results thus obtained are shown in Table 1.

Example 6

0.1 moles of oxalic acid dihydrate, 0.2 moles of zirconium oxychloride octahydrate containing 0.15% of hafnium, and 0.03 moles of ammonium chloride were dissolved in 300 mL of deionized water, and 0.3 moles of phosphoric acid were added thereto while stirring. The pH of this solution was adjusted to 2.2 using a 20% aqueous sodium hydroxide solution, and the solution was then stirred at 98° C. for 6 hours. Subsequently, the precipitate thus obtained was washed well and dried at 120° C. to synthesize a zirconium phosphate compound.

Respective component amounts of this zirconium phosphate compound were measured and a composition formula thereof was obtained as follows:

$$Na_{0.64}(NH_4)_{0.22}H_{0.10}Zr_{1.99}Hf_{0.02}(PO_4)_3 \cdot 0.11H_2O$$

450 ml of a 1N nitric acid solution obtained by dissolving 0.05 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 120 μS, and the resulting solid was dried at 120° C. and bulk specific gravity thereof was adjusted to 1.20.

Respective components of the dried solid composed of the silver-supported zirconium phosphate were measured and the resulting composition formula was given as follows:

$$Ag_{0.55}Na_{0.15}(NH_4)_{0.20}H_{0.06}Zr_{1.99}Hf_{0.02}(PO_4)_3 \cdot 0.20H_2O$$

In addition, the dried product was treated using a gas furnace at 850° C. for 24 hours to perform thermal decomposition. After thermal decomposition, the powder X-ray diffraction pattern of the silver-supporting zirconium phosphate was measured. As a result, the relative intensity at a peak of 2θ=21.4, indicating zirconium pyrophosphate, with the respect to X-ray intensity at 2θ=20.1, indicating the zirconium phosphate compound, was 22. This powder was pulverized to obtain a silver-based inorganic antimicrobial agent of the present invention.

The median diameter (μm), maximum particle size (μm), and minimum concentration of growth inhibition to *E. coli* (MIC, μg/ml) of the silver-based antimicrobial agent were measured and the results thus obtained are shown in Table 1.

Example 7

0.1 moles of oxalic acid dihydrate and 0.2 moles of zirconium oxychloride octahydrate containing 0.15% of hafnium were dissolved in 300 mL of deionized water, and 0.3 moles of phosphoric acid was added thereto while stirring. The pH of this solution was adjusted to 2.2 using a 20% aqueous sodium hydroxide solution, and the solution was then stirred at 98° C. for 6 hours. Subsequently, the precipitate thus obtained was washed well and dried at 120° C. to synthesize a zirconium phosphate compound.

Respective component amounts of this zirconium phosphate compound were measured and a composition formula thereof was obtained as follows:

$$Na_{0.96}Zr_{1.99}Hf_{0.02}(PO_4)_3 \cdot 0.10H_2O$$

450 ml of a 1N nitric acid solution obtained by dissolving 0.02 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 90 μS, and the resulting solid was dried at 120° C. and bulk specific gravity thereof was adjusted to 1.15.

Respective components of the dried solid composed of the silver-supported zirconium phosphate were measured and the resulting composition formula was given as follows:

$$Ag_{0.21}Na_{0.38}H_{0.37}Zr_{1.99}Hf_{0.02}(PO_4)_3 \cdot 0.11H_2O$$

Furthermore, the dried product was treated using a gas furnace at 850° C. for 12 hours to perform thermal decomposition. After thermal decomposition, the powder X-ray diffraction pattern of the silver-supporting zirconium phosphate was measured. As a result, the relative intensity at a peak of 2θ=21.4, indicating zirconium pyrophosphate, with respect to the X-ray intensity at 2θ=20.1, indicating the zirconium phosphate compound, was 15. This powder was pulverized to obtain a silver-based inorganic antimicrobial agent of the present invention.

The median diameter (μm), maximum particle size (μm), and minimum concentration of growth inhibition to *E. coli* (MIC, μg/ml) of the silver-based antimicrobial agent were measured and the results thus obtained are shown in Table 1.

Comparative Example 1

0.1 moles of oxalic acid dihydrate and 0.2 moles of zirconium oxychloride octahydrate containing 0.17% of hafnium and 0.1 moles of ammonium chloride were dissolved in 300 mL of deionized water, and 0.3 moles of phosphoric acid was added thereto while stirring. The pH of this solution was adjusted to 2.6 using a 20% aqueous sodium hydroxide solution, and the solution was then stirred at 98° C. for 14 hours. Subsequently, the precipitate thus obtained was washed well and dried at 120° C. to synthesize a zirconium phosphate compound.

Respective component amounts of this zirconium phosphate compound were measured and a composition formula thereof was obtained as follows:

$$Na_{0.6}(NH_4)_{0.4}Zr_{1.98}Hf_{0.02}(PO_4)_3 \cdot 0.09H_2O$$

450 ml of an aqueous solution of deionized water obtained by dissolving 0.05 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 190 μS, and the resulting solid was dried at 120° C.

Respective components of the dried solid composed of the silver-supported zirconium phosphate were measured and the resulting composition formula was given as follows:

$$Ag_{0.55}Na_{0.05}(NH_4)_{0.4}Zr_{1.98}Hf_{0.02}(PO_4)_3 \cdot 0.10H_2O$$

The powder X-ray diffraction pattern of the silver-supporting zirconium phosphate was measured. As a result, there was no peak of 2θ=21.4, indicating zirconium pyrophosphate and relative intensity was zero. The powder was pulverized to obtain the antimicrobial agent of Comparative Example 1. The median diameter (μm), maximum particle size (μm), and minimum concentration of growth inhibition to *E. coli* (MIC, μg/ml) of the antimicrobial agent were measured and the results thus obtained are shown in Table 1.

Comparative Example 2

0.1 moles of oxalic acid dihydrate and 0.2 moles of zirconium oxychloride octahydrate containing 0.17% of hafnium and 0.1 moles of ammonium chloride were dissolved in 300 mL of deionized water, and 0.3 moles of phosphoric acid was added thereto while stirring. The pH of this solution was adjusted to 2.6 using a 20% aqueous sodium hydroxide solution, and the solution was then stirred at 98° C. for 14 hours. Subsequently, the precipitate thus obtained was washed well and dried at 120° C. to synthesize a zirconium phosphate compound.

Respective component amounts of this zirconium phosphate compound were measured and a composition formula thereof was obtained as follows:

$$Na_{0.6}(NH_4)_{0.4}Zr_{1.98}Hf_{0.02}(PO_4)_3 \cdot 0.09H_2O$$

450 ml of an aqueous solution of deionized water obtained by dissolving 0.05 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 340 μS, and the resulting solid was dried at 120° C. and bulk specific gravity thereof was adjusted to 1.03.

Respective components of the dried solid composed of the silver-supported zirconium phosphate were measured and the resulting composition formula was given as follows:

$$Ag_{0.55}Na_{0.05}(NH_4)_{0.40}Zr_{1.98}Hf_{0.02}(PO_4)_3 \cdot 0.09H_2O$$

Then, the dried product was treated using a gas furnace at 1,100° C. for 12 hours to perform thermal decomposition. The powder X-ray diffraction pattern of the silver-supporting zirconium phosphate after thermal decomposition was measured. As a result, the relative intensity at a peak of 2θ=21.4, indicating zirconium pyrophosphate, with respect to the X-ray intensity at 2θ=20.1, indicating the zirconium phosphate compound, was 55. This powder was pulverized to obtain the silver-based inorganic antimicrobial agent of Comparative Example 2. The median diameter (μm), maximum particle size (μm), and minimum concentration of growth inhibition to E. coli (MIC, μg/ml) of the silver-based antimicrobial agent were measured and the results thus obtained are shown in Table 1.

Comparative Example 3

0.1 moles of oxalic acid dihydrate and 0.2 moles of zirconium oxychloride octahydrate containing 0.17% of hafnium and 0.1 moles of ammonium chloride were dissolved in 300 mL of deionized water, and 0.3 moles of phosphoric acid was added thereto while stirring. The pH of this solution was adjusted to 2.6 using a 20% aqueous sodium hydroxide solution, and the solution was then stirred at 98° C. for 14 hours. Subsequently, the precipitate thus obtained was washed well and dried at 120° C. to synthesize a zirconium phosphate compound.

Respective component amounts of this zirconium phosphate compound were measured and a composition formula thereof was obtained as follows:

$$Na_{0.6}(NH_4)_{0.4}Zr_{1.98}Hf_{0.02}(PO_4)_3 \cdot 0.09H_2O$$

450 ml of an aqueous solution of deionized water obtained by dissolving 0.05 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 770 μS, and the resulting solid was dried at 120° C. and bulk specific gravity thereof was adjusted to 1.16.

Respective components of the dried solid composed of the silver-supported zirconium phosphate were measured and the resulting composition formula was given as follows:

$$Ag_{0.55}Na_{0.05}(NH_4)_{0.40}Zr_{1.98}Hf_{0.02}(PO_4)_3 \cdot 0.19H_2O$$

Then, the dried product was treated using a gas furnace at 1,150° C. for 4 hours to perform thermal decomposition. The powder X-ray diffraction pattern of the silver-supporting zirconium phosphate after thermal decomposition was measured. As a result, the relative intensity at a peak of 2θ=21.4, indicating zirconium pyrophosphate, with respect to the X-ray intensity at 2θ=20.1, indicating the zirconium phosphate compound, was 55. This powder was pulverized to obtain the silver-based inorganic antimicrobial agent of Comparative Example 2. The median diameter (μm), maximum particle size (μm), and minimum concentration of growth inhibition to E. coli (MIC, μg/ml) of the silver-based antimicrobial agent were measured and the results thus obtained are shown in Table 1.

Comparative Example 4

0.1 moles of oxalic acid dihydrate and 0.2 moles of zirconium oxychloride octahydrate containing 0.17% of hafnium and 0.1 moles of ammonium chloride were dissolved in 300 mL of deionized water, and 0.3 moles of phosphoric acid was added thereto while stirring. The pH of this solution was adjusted to 2.6 using a 20% aqueous sodium hydroxide solution, and the solution was then stirred at 98° C. for 8 hours. Subsequently, the precipitate thus obtained was washed well and dried at 120° C. to synthesize a zirconium phosphate compound.

Respective component amounts of this zirconium phosphate compound were measured and a composition formula thereof was obtained as follows:

$$Na_{1.0}Zr_{1.08}Hf_{0.02}(PO_4)_3 \cdot 0.09H_2O$$

450 ml of an aqueous solution of deionized water obtained by dissolving 0.05 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 190 μS, and the resulting solid was dried at 120° C. and bulk specific gravity thereof was adjusted to 0.82.

Respective components of the dried solid composed of the silver-supported zirconium phosphate were measured and the resulting composition formula was given as follows:

$$Ag_{0.55}Na_{0.05}H_{0.40}Zr_{1.95}Hf_{0.02}(PO_4)_3 \cdot 0.17H_2O$$

Then, the dried product was treated using a gas furnace at 800° C. for 2 hours to perform thermal decomposition. The powder X-ray diffraction pattern of the silver-supporting zirconium phosphate after thermal decomposition was measures. As a result, the relative intensity at a peak of 2θ=21.4, indicating zirconium pyrophosphate, with respect to the X-ray intensity at 2θ=20.1, indicating the zirconium phosphate compound, was 3. This powder was pulverized to obtain the silver-based inorganic antimicrobial agent of Comparative Example 4. The median diameter (μm), maximum particle size (μm), and minimum concentration of growth inhibition to E. coli (MIC, μg/ml) of the silver-based antimicrobial agent were measured and the results thus obtained are shown in Table 1.

Comparative Example 5

0.1 moles of oxalic acid dihydrate and 0.2 moles of zirconium oxychloride octahydrate containing 0.17% of hafnium and 0.1 moles of ammonium chloride were dissolved in 300 mL of deionized water, and 0.3 moles of phosphoric acid was added thereto while stirring. The pH of this solution was adjusted to 2.6 using a 20% aqueous sodium hydroxide solution, and the solution was then stirred at 98° C. for 8 hours. Subsequently, the precipitate thus obtained was washed well and dried at 120° C. to synthesize a zirconium phosphate compound.

Respective component amounts of this zirconium phosphate compound were measured and a composition formula thereof was obtained as follows:

$$Na_{1.0}Zr_{1.98}Hf_{0.02}(PO_4)_3 \cdot 0.09H_2O$$

450 ml of an aqueous solution of deionized water obtained by dissolving 0.05 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 175 µS, and the resulting solid was dried at 120° C. and bulk specific gravity thereof was adjusted to 0.44.

Respective components of the dried solid composed of the silver-supported zirconium phosphate were measured and the resulting composition formula was given as follows:

$$Ag_{0.55}Na_{0.05}H_{0.55}Zr_{1.98}Hf_{0.02}(PO_4)_3 \cdot 0.21H_2O$$

Then, the dried product was treated using a gas furnace at 900° C. for 2 hours to perform thermal decomposition. The powder X-ray diffraction pattern of the silver-supporting zirconium phosphate after thermal decomposition was measured. As a result, the relative intensity at a peak of 2θ=21.4, indicating zirconium pyrophosphate, with respect to the X-ray intensity at 2θ=20.1, indicating the zirconium phosphate compound, was 52. This powder was pulverized to obtain the silver-based inorganic antimicrobial agent of Comparative Example 5. The median diameter (µm), maximum particle size (µm) and minimum concentration of growth inhibition to *E. coli* (MIC, µg/ml) were measured and the results thus obtained are shown in Table 1.

Comparative Example 6

0.1 moles of oxalic acid dihydrate and 0.2 moles of zirconium oxychloride octahydrate containing 0.15% of hafnium were dissolved in 300 mL of deionized water, and 0.3 moles of phosphoric acid was added thereto while stirring. The pH of this solution was adjusted to 2.2 using a 20% aqueous sodium hydroxide solution, and the solution was then stirred at 98° C. for 6 hours. Subsequently, the precipitate thus obtained was washed well and dried at 120° C. to synthesize a zirconium phosphate compound.

Respective component amounts of this zirconium phosphate compound were measured and a composition formula thereof was obtained as follows:

$$Na_{0.96}Zr_{1.99}Hf_{0.02}(PO_4)_3 \cdot 0.10H_2O$$

450 ml of an 1N aqueous nitric acid solution obtained by dissolving 0.02 moles of silver nitrate was added to 0.09 moles of zirconium phosphate thus obtained, followed by stirring at 60° C. for 2 hours, to support silver. After the silver-supporting process, the resulting slurry was filtered and washed with water, the filtrate was washed until the electrical conductivity of the filtrate reached 660 µS, and the resulting solid was dried at 120° C. and bulk specific gravity thereof was adjusted to 0.51.

Respective components of the dried solid composed of the silver-supported zirconium phosphate were measured and the resulting composition formula was given as follows:

$$Ag_{0.21}Na_{0.38}H_{0.37}Zr_{1.99}Hf_{0.02}(PO_4)_3 \cdot 0.10H_2O$$

Then, the dried product was treated using a gas furnace at 750° C. for 48 hours to perform thermal decomposition. The powder X-ray diffraction pattern of the silver-supporting zirconium phosphate after thermal decomposition was measured. As a result, the relative intensity at a peak of 2θ=21.4, indicating zirconium pyrophosphate, with respect to the X-ray intensity at 2θ=20.1, indicating the zirconium phosphate compound, was 4. This powder was pulverized to obtain the silver-based inorganic antimicrobial agent of Comparative Example 6. The median diameter (µm), maximum particle size (µm) and minimum concentration of growth inhibition to *E. coli* (MIC, µg/ml) of the silver-based antimicrobial agent were measured and the results thus obtained are shown in Table 1.

TABLE 1

|  | Electrical conductivity (µS) | Bulk specific gravity (g/ml) | Thermal decomposition temperature (° C.) | Thermal decomposition time (hour) |
|---|---|---|---|---|
| Ex.1 | 220 | 1.21 | 900 | 12 |
| Ex.2 | 380 | 1.00 | 900 | 9 |
| Ex.3 | 80 | 1.30 | 800 | 24 |
| Ex.4 | 240 | 1.25 | 1000 | 6 |
| Ex.5 | 210 | 1.16 | 850 | 24 |
| Ex.6 | 120 | 1.12 | 950 | 4 |
| Ex.7 | 90 | 1.15 | 850 | 12 |
| Comp. Ex.1 | 190 | — | — | — |
| Comp. Ex.2 | 340 | 1.03 | 1100 | 12 |
| Comp. Ex.3 | 770 | 1.16 | 1150 | 4 |
| Comp. Ex.4 | 190 | 0.82 | 800 | 2 |
| Comp. Ex.5 | 175 | 0.44 | 900 | 16 |
| Comp. Ex.6 | 660 | 0.51 | 750 | 48 |

In the above table, "—" means not measured.

TABLE 2

|  | X-ray relative intensity | Median diameter (µm) | Maximum particle size (µm) | MIC (µg/ml) | Concentration of eluted silver (ppm) |
|---|---|---|---|---|---|
| Ex.1 | 22 | 1.1 | 2.4 | 25 | 2.6 |
| Ex.2 | 18 | 1.0 | 3.8 | 25 | 2.1 |
| Ex.3 | 8 | 0.9 | 2.1 | 25 | 2.7 |
| Ex.4 | 42 | 1.6 | 3.8 | 50 | 3.6 |
| Ex.5 | 22 | 1.2 | 2.3 | 25 | 2.4 |
| Ex.6 | 28 | 1.2 | 2.2 | 25 | 2.9 |
| Ex.7 | 15 | 1.0 | 1.8 | 100 | 1.5 |
| Comp. Ex.1 | 0 | 0.9 | 1.4 | 25 | 12.2 |
| Comp. Ex.2 | 55 | 1.9 | 5.7 | 50 | 7.6 |
| Comp. Ex.3 | 55 | 1.8 | 6.1 | 50 | 7.9 |
| Comp. Ex.4 | 3 | 2.3 | 4.4 | 25 | 7.9 |
| Comp. Ex.5 | 52 | 2.8 | 4.1 | 25 | 8.2 |
| Comp. Ex.6 | 4 | 0.9 | 1.9 | 100 | 5.7 |

As is apparent from the results of Table 2, the silver-based inorganic antimicrobial agents of Examples 1 to 7 exhibit a similar particle size, superior antimicrobial property (MIC) and a reduced eluted silver amount, as compared to Comparative Examples.

Example 8

Evaluation of Photosetting Resin

3% of each silver-based inorganic antimicrobial agent obtained in Examples 1 to 7 and Comparative Examples 1 to 6 was mixed with a photosetting resin, coated to a thickness of about 2 microns on a PET film, and cured to prepare an antimicrobial hard coat film. In addition, for comparison, a blank hard coat film containing no antimicrobial agent was prepared in the same manner. Facilitation of the evenness of coating part of the hard coat film thus obtained and the results confirmed by SEM observation are shown in Table 2. In addition, the unmodified hard coat film was dipped in 25° C. deionized water for 16 hours, and the coating surface was subjected to antimicrobial tests using *E. coli* in accordance with a plastic product test method such as JIS Z2801 5.2. The results of the antimicrobially activity value thus obtained are shown in Table 3. In addition, the antimicrobial activity value is a value which indicates a difference in number of living microbes between antimicrobial products and non-antimicrobial products after tests and has no unit. Commonly, when the antimicrobially activity value is 2.0 or more, the antimicrobial processing effect is recognized as occurring.

TABLE 3

| | | Antimicrobially activity value | |
|---|---|---|---|
| | Evenness | Not treated | After waterproof test |
| Antimicrobial hard coat film A (Ex.1) | Even | Greater than 5.1 | Greater than 5.1 |
| Antimicrobial hard coat film B (Ex.2) | Even | Greater than 5.1 | Greater than 5.1 |
| antimicrobial hard coat film C (Ex.3) | Even | Greater than 5.1 | Greater than 5.1 |
| Antimicrobial hard coat film D (Ex.4) | Even | Greater than 5.1 | Greater than 5.1 |
| Antimicrobial hard coat film E (Ex.5) | Even | Greater than 5.1 | Greater than 5.1 |
| Antimicrobial hard coat film F (Ex.6) | Even | Greater than 5.1 | Greater than 5.1 |
| Antimicrobial hard coat film G (Ex.7) | Even | Greater than 5.1 | 4.6 |
| Antimicrobial hard coat film a (Comp. Ex.1) | Even | Greater than 5.1 | 0.9 |
| Antimicrobial hard coat film b (Comp. Ex.2) | Rough | Greater than 5.1 | 2.9 |
| Antimicrobial hard coat film c (Comp. Ex.3) | Rough | Greater than 5.1 | 2.5 |
| Antimicrobial hard coat film d (Comp. Ex.4) | Rough | Greater than 5.1 | 1.1 |
| Antimicrobial hard coat film e (Comp. Ex.5) | Rough | Greater than 5.1 | 1.1 |
| Antimicrobial hard coat film f (Comp. Ex.6) | Even | 5.0 | 0.8 |

Example 9

Evaluation in Nylon Threads

1% of each silver-based inorganic antimicrobial agent obtained in Examples 1 and 7, and Comparative Examples 1, 2 and 6 was mixed with a nylon resin and nylon multi-filaments of about 3 deniers were spun. The state of thread breakage during spinning and color tone after spinning are shown in Table 3. In addition, a thread breakage test was evaluated according to whether or not threads were broken until one package having 6 kg of wound unstretched threads was obtained. A color tone was obtained by measuring color values of threads after spinning using a Σ80 type colormetric color-difference meter manufactured by Nippon Electric Industry Co., Ltd. and was represented by a Hunter Lab color coordinate system in accordance with JIS Z8730-1980, and color difference ΔE (delta E) was calculated by comparison with blank threads. The antimicrobial property of antimicrobial nylon multi-filaments was evaluated by subjecting untreated (unwashed) multi-filaments and multi-filaments which underwent washing 10 times to an antimicrobial property test of fiber products in accordance with JIS L1902 and the results of antimicrobial activity value thus obtained are shown in Table 4.

TABLE 4

| | | | Antimicrobially activity value | |
|---|---|---|---|---|
| | Thread breakage | ΔE | Not treated | After washing 10 times |
| Fiber a (Ex.1) | Absent | 1.8 | Greater than 5.1 | 3.4 |
| Fiber b (Ex.7) | Absent | 1.2 | Greater than 5.1 | 2.3 |
| Comparative fiber c (Comp. Ex.1) | Absent | 6.7 | Greater than 5.1 | 0.7 |
| Comparative fiber d (Comp. Ex.2) | Present | 2.5 | Greater than 5.1 | 1.9 |
| Comparative fiber e (Comp. Ex.6) | Absent | 1.0 | 4.9 | 1.4 |

Example 10

Evaluation in Urethane Foam Body 100 parts of a mixture of polyetherpolyol, triethylenediamine, water, methylene chloride, a blowing agent, a catalyst, toluene isocyanate and zinc oxide was mixed with 0.7 parts of the silver-based inorganic antimicrobial agent prepared in Example 1 to prepare an antimicrobial urethane foam body A.

Similarly, antimicrobial urethane foam bodies B and C and antimicrobial urethane foam bodies d to f for comparison were produced using silver-based inorganic antimicrobial agents for comparison prepared in Examples 2 and 3 and Comparative Examples 1 to 3. The antimicrobial urethane foam bodies and antimicrobial urethane foam bodies which were subjected to dipping at 50° C. in deionized water for 16 hours, dried and waterproofed were subjected to an antimicrobial test in accordance with a shaking method of Antimicrobial Product technology Association using *Staphylococcus aureus* and *E. coli*. to measure antimicrobial activity values, and the results thus obtained are shown in Table 5.

TABLE 5

| | Antimicrobial activity value of *Staphylococcus aureus* | | Antimicrobial activity value of *E. coli*. | |
|---|---|---|---|---|
| | Not treated | Waterproofed | Not treated | Waterproofed |
| Antimicrobial urethane foam body A (Ex. 1) | Greater than 2.8 | Greater than 2.8 | Greater than 5.1 | Greater than 5.1 |
| Antimicrobial urethane foam body B (Ex. 2) | Greater than 2.8 | Greater than 2.8 | Greater than 5.1 | 4.9 |
| Antimicrobial urethane foam body C (Ex. 3) | 2.6 | 2.2 | Greater than 5.1 | 4.2 |
| Comparative antimicrobial urethane foam body d (Comp. Ex. 1) | 2.5 | 1.2 | Greater than 5.1 | 2.2 |

TABLE 5-continued

| | Antimicrobial activity value of *Staphylococcus aureus* | | Antimicrobial activity value of *E. coli*. | |
|---|---|---|---|---|
| | Not treated | Waterproofed | Not treated | Waterproofed |
| Comparative antimicrobial urethane foam body e (Comp. Ex. 2) | 2.1 | 1.8 | 4.1 | 2.0 |
| Comparative antimicrobial urethane foam body f (Comp. Ex. 3) | 2.1 | 1.1 | 3.2 | 1.9 |

It can be seen from these results that the silver-based inorganic antimicrobial agent of the present invention exhibits a superior antimicrobial property after the waterproof test, as well as excellent processability or discoloration resistance when mixed with plastic products.

INDUSTRIAL APPLICABILITY

The novel silver-based inorganic antimicrobial agent of the present invention is composed of uniform and fine particles and thus exhibits superior processability and plastic products manufactured therefrom exhibit a long-lasting antimicrobial property after the waterproof test. Accordingly, the present invention may be useful as a silver-based inorganic antimicrobial agent which is highly applicable to products which are frequently exposed to water.

What is claimed is:

1. A silver-based inorganic antimicrobial agent represented by Formula (1) below containing zirconium pyrophosphate ($ZrP_2O_7$) wherein, in the powder X-ray diffraction pattern, a relative intensity of an X-ray diffraction peak at $2\theta=21.3°$ to $21.5°$ is 5 to 50, based on 100 of an X-ray diffraction peak intensity at $2\theta=20.0°$ to $20.2°$:

$$Ag_aM_bZr_cHf_d(PO_4)_3 \cdot nH_2O \qquad (1)$$

wherein M is at least one ion selected from an alkali metal ion, an ammonium ion, a hydrogen ion and an oxonium ion, a, b, c and d are positive numbers satisfying $1.75<(c+d)<2.2$ and $a+b+4(c+d)=9$, and n is 2 or less.

2. A method for producing the silver-based inorganic antimicrobial agent represented by Formula (1) below containing zirconium pyrophosphate ($ZrP_2O_7$):

$$Ag_aM_bZr_cHf_d(PO_4)_3 \cdot nH_2O \qquad (1)$$

wherein M is at least one ion selected from an alkali metal ion, an ammonium ion, a hydrogen ion and an oxonium ion, a, b, c and d are positive numbers satisfying $1.75<(c+d)<2.2$ and $a+b+4(c+d)=9$, and n is 2 or less, comprising:

a step of obtaining a silver-based inorganic antimicrobial agent represented by Formula (1) by wet-synthesis or hydrothermal synthesis, and a step of thermally decomposing the antimicrobial agent at 800° C. to 1,100° C., wherein the silver-based inorganic antimicrobial agent has an electrical conductivity of 15 µS to 570 µS when suspended in water, and wherein the silver-based inorganic antimicrobial agent has a bulk specific gravity before thermal decomposition of 0.80 to 2.00 (g/ml).

3. A waterproof antimicrobial product comprising the silver-based inorganic antimicrobial agent according to claim 1.

4. The silver-based inorganic antimicrobial agent according to claim 1, wherein a is at least 0.01 and not greater than 1.

5. The silver-based inorganic antimicrobial agent according to claim 1, wherein b is at least 0.001 and less than 1.

6. The silver-based inorganic antimicrobial agent according to claim 1, wherein M is at least one ion selected from the group consisting of a sodium ion, a potassium ion, an ammonium ion, and a hydrogen ion.

7. The silver-based inorganic antimicrobial agent according to claim 1, wherein n is in a range of 0.01 to 0.5.

8. The method for producing the silver-based inorganic antimicrobial agent according to claim 2, wherein the method comprises the step of thermally decomposing the antimicrobial agent at 820° C. to 1,050° C.

9. The method for producing the silver-based inorganic antimicrobial agent according to claim 2, wherein the step comprises the step of thermally decomposing the antimicrobial agent at 820° C. to 1,050° C. for 2 to 60 hours.

10. The method for producing the silver-based inorganic antimicrobial agent according to claim 2, wherein a is at least 0.01 and not greater than 1.

11. The method for producing the silver-based inorganic antimicrobial agent according to claim 2, wherein b is at least 0.001 and less than 1.

12. The method for producing the silver-based inorganic antimicrobial agent according to claim 2, wherein M is at least one ion selected from the group consisting of a sodium ion, a potassium ion, an ammonium ion, and a hydrogen ion.

13. The method for producing the silver-based inorganic antimicrobial agent according to claim 2, wherein n is in the range of 0.01 to 0.5.

14. The method for producing the silver-based inorganic antimicrobial agent according to claim 2, wherein, in the powder X-ray diffraction pattern, a relative intensity of an X-ray diffraction peak at $2\theta=21.3°$ to $21.5°$ is 5 to 50, based on 100 of an X-ray diffraction peak intensity at $2\theta=20.0°$ to $20.2°$.

15. The waterproof antimicrobial product according to claim 3, wherein the product is in a form of urethane form body.

16. The waterproof antimicrobial product according to claim 3, wherein the product is in a form of nylon threads.

17. The waterproof antimicrobial product according to claim 3, wherein the product is in a form of hard coat film.

* * * * *